(12) United States Patent
Smith et al.

(10) Patent No.: US 8,722,353 B2
(45) Date of Patent: May 13, 2014

(54) ANALYTICAL METHOD FOR FAB AND FAB' MOLECULES

(75) Inventors: Bryan John Smith, Slough (GB); Helen Marie Kirke, Slough (GB)

(73) Assignee: UCB Pharma, S.A., Brussels (BE)

( * ) Notice: Subject to any disclaimer, the term of this patent is extended or adjusted under 35 U.S.C. 154(b) by 0 days.

(21) Appl. No.: 13/812,692

(22) PCT Filed: Jul. 28, 2011

(86) PCT No.: PCT/GB2011/001135
§ 371 (c)(1),
(2), (4) Date: Apr. 3, 2013

(87) PCT Pub. No.: WO2012/013933
PCT Pub. Date: Feb. 2, 2012

(65) Prior Publication Data
US 2013/0183703 A1    Jul. 18, 2013

(30) Foreign Application Priority Data
Jul. 29, 2010 (GB) .................................. 1012784.3

(51) Int. Cl.
*C12Q 1/37* (2006.01)
(52) U.S. Cl.
USPC .......................................................... 435/23
(58) Field of Classification Search
USPC .......................................................... 435/23
See application file for complete search history.

(56) References Cited

FOREIGN PATENT DOCUMENTS

WO    WO 2005/059106    6/2005
WO    WO 2008/025528    3/2008

OTHER PUBLICATIONS

Teshima, G. "Deamidation in Proteins and Peptides" IonSource.com, Nov. 21, 2000, pp. 1-8, XP002665740.
Huang, H. Z. et al. "Direct Identification and Quantification of Aspartyl Succinimide in an IgG2 mAb by RapiGest Assisted Digestion" *Analytical Chemistry*, Feb. 15, 2009, pp. 1686-1692, vol. 81, No. 4.
Yang, H. et al. "Mass spectrometric analysis of asparagine deamidation and aspartate isomerization in polypeptides" *Electrophoresis*, Jun. 1, 2010, pp. 1764-1772, vol. 31, No. 11.
Chelius, D. et al. "Identification and Characterization of Deamidation Dites in the Conserved Regions of Human Immunoglobulin Gamma Antibodies" *Analytical Chemistry*, Sep. 15, 2005, pp. 6004-6011, vol. 77, No. 18.
Kroon, D. et al. "Identification of Sites of Degradation in a Therapeutic Monoclonal Antibody by Peptide Mapping" *Pharmaceutical Research*, Nov. 1, 1992, pp. 1386-1393, vol. 9, No. 11.
Leong, S. et al. "Adapting pharmacokinetic properties of a humanized anti-interleukin-8 antibody for therapeutic applications using site-specific pegylation" *Cytokine*, Nov. 7, 2001, pp. 106-119, vol. 16, No. 3.
Written Opinion in International Application No. PCT/GB2011/001135, Jan. 3, 2012, pp. 1-7.

*Primary Examiner* — Ralph Gitomer
(74) *Attorney, Agent, or Firm* — Saliwanchik, Lloyd & Eisenschenk

(57) ABSTRACT

A method of measuring acidic species generated by degradation of a Fab or Fab' component of a Fab-PEG or a Fab'-PEG is provided. The method involves: a) cleaving PEG and a linker from the Fab-PEG or Fab'-PEG with an enzyme; b) optionally separating the PEG and linker from the Fab or Fab' to provide isolated Fab or Fab'; and c) quantitatively analyzing acidic species associated with the cleaved Fab or Fab' and/or the cleaved PEG.

10 Claims, 11 Drawing Sheets

Figure 1 Schematic diagram of a PEGylated Fab' format.

Figure 2 Schematic diagram of a PEGylated Fab' format with deamidation in the Fab' fragment Figure 3 Schematic diagram of a PEGylated Fab' format with deamidation in the Fab' fragment and hydrolysis of the linker to generate acidic species Figure 4 Schematic representation of the hydrolysis of Fab' and PEG maleimide followed by ring opening of the PEG linker succinimide ring Analysis of combined acidic species, linker hydrolysis generated acidic species and acidic species generated through deamidation

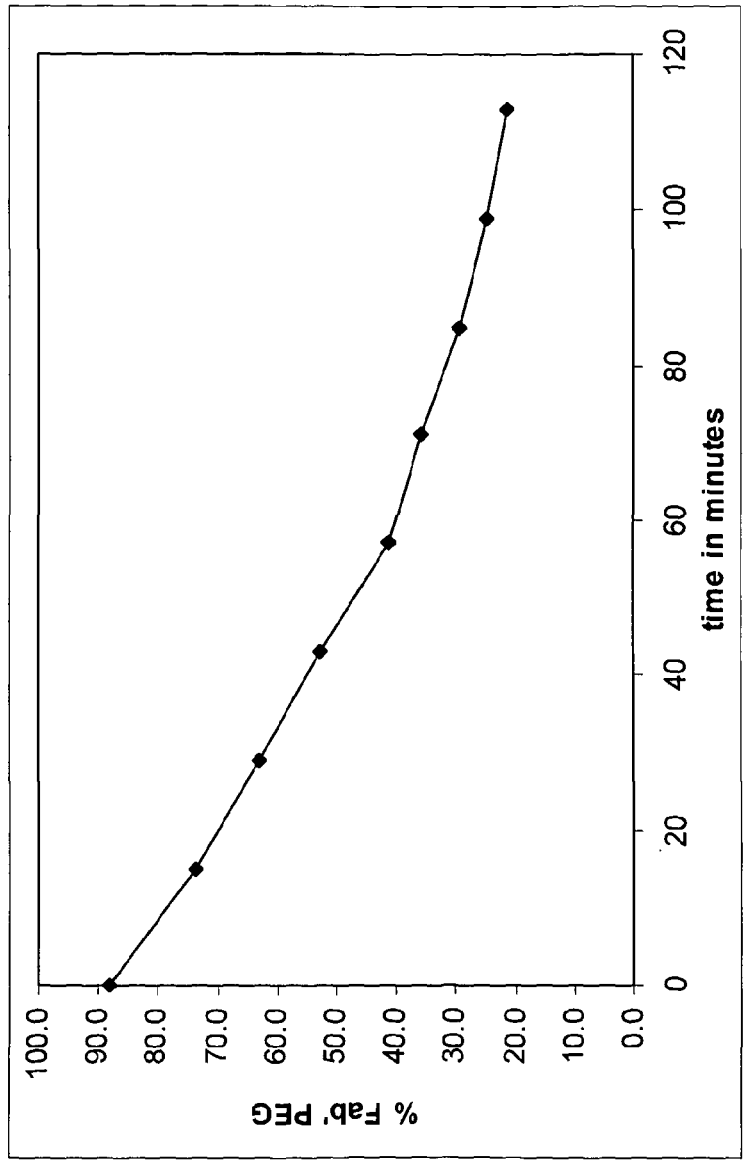
Figure 7 Efficiency of Tryptic Digest Conditions followed by HTRP HPLC

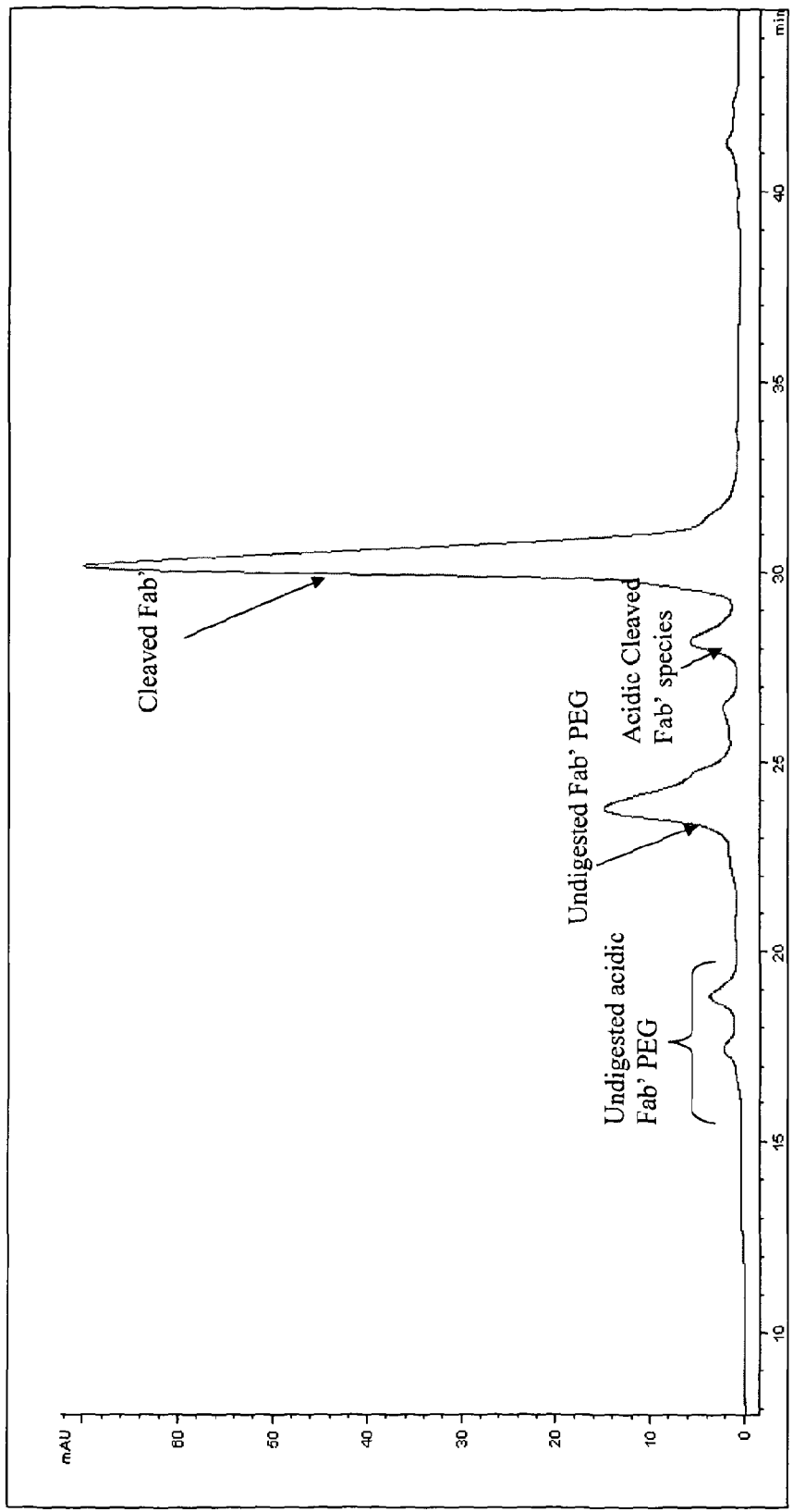
Figure 8 Fab' PEG CEX HPLC digest profile

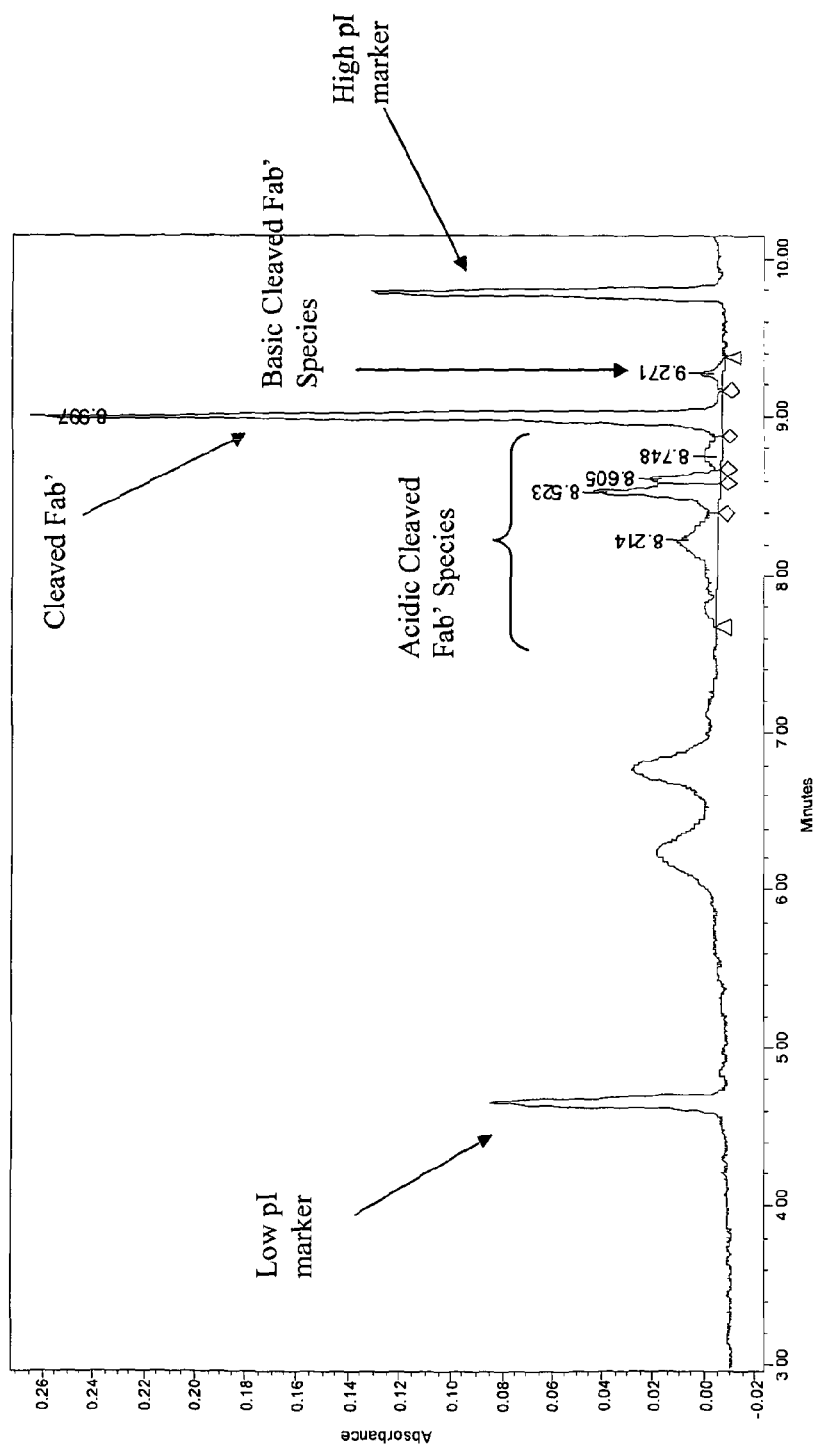
Figure 9 cIEF profile of tryptic digest of Fab' PEG

Figure 10

SEQ ID NO: 1 shows the amino acid sequence of CDRH1 of CDP870.
Asp Tyr Gly Met Asn SEQ ID NO: 2 shows the amino acid sequence of CDRH2 of CDP870
Trp Ile Asn Thr Tyr Ile Gly Glu Pro Ile Tyr Ala Asp Ser Val Lys Gly SEQ ID NO: 3 shows the amino acid sequence of CDRH3 of CDP870.
Gly Tyr Arg Ser Tyr Ala Met Asp Tyr SEQ ID NO: 4 shows the amino acid sequence of CDRL1 of CDP870.
Lys Ala Ser Gln Asn Val Gly Thr Asn Val Ala SEQ ID NO: 5 shows the amino acid sequence of CDRL2 of CDP870.
Ser Ala Ser Phe Leu Tyr Ser SEQ ID NO: 6 shows the amino acid sequence of CDRL3 of CDP870.
Gln Gln Tyr Asn Ile Tyr Pro Leu Thr SEQ ID NO: 7 shows the amino acid sequence of the light chain variable region CDP870
Asp Ile Gln Met Thr Gln Ser Pro Ser Ser Leu Ser Ala Ser Val Gly Asp Arg Val Thr Ile Thr Cys
Lys Ala Ser Gln Asn Val Gly Thr Asn Val Ala Trp Tyr Gln Gln Lys Pro Gly Lys Ala Pro Lys Ala
Leu Ile Tyr Ser Ala Ser Phe Leu Tyr Ser Gly Val Pro Tyr Arg Phe Ser Gly Ser Gly Ser Gly Thr
Asp Phe Thr Leu Thr Ile Ser Ser Leu Gln Pro Glu Asp Phe Ala Thr Tyr Tyr Cys Gln Gln Tyr Asn
Ile Tyr Pro Leu Thr Phe Gly Gln Gly Thr Lys Val Glu Ile Lys SEQ ID NO:8 shows the amino acid sequence of the heavy chain variable region CDP870.
Glu Val Gln Leu Val Glu Ser Gly Gly Gly Leu Val Gln Pro Gly Gly Ser Leu Arg Leu Ser Cys Ala
Ala Ser Gly Tyr Val Phe Thr Asp Tyr Gly Met Asn Trp Val Arg Gln Ala Pro Gly Lys Gly Leu Glu
Trp Met Gly Trp Ile Asn Thr Tyr Ile Gly Glu Pro Ile Tyr Ala Asp Ser Val Lys Gly Arg Phe Thr
Phe Ser Leu Asp Thr Ser Lys Ser Thr Ala Tyr Leu Gln Met Asn Ser Leu Arg Ala Glu Asp Thr Ala
Val Tyr Tyr Cys Ala Arg Gly Tyr Arg Ser Tyr Ala Met Asp Tyr Trp Gly Gln Gly Thr Leu Val Thr
Val Ser Ser

Figure 11

SEQ ID NO: 9 shows the amino acid sequence of a grafted anti-TNFα Fab CDP870 light chain.
Asp Ile Gln Met Thr Gln Ser Pro Ser Ser Leu Ser Ala Ser Val Gly Asp Arg Val Thr Ile Thr Cys
Lys Ala Ser Gln Asn Val Gly Thr Asn Val Ala Trp Tyr Gln Gln Lys Pro Gly Lys Ala Pro Lys Ala
Leu Ile Tyr Ser Ala Ser Phe Leu Tyr Ser Gly Val Pro Tyr Arg Phe Ser Gly Ser Gly Ser Gly Thr
Asp Phe Thr Leu Thr Ile Ser Ser Leu Gln Pro Glu Asp Phe Ala Thr Tyr Tyr Cys Gln Gln Tyr Asn
Ile Tyr Pro Leu Thr Phe Gly Gln Gly Thr Lys Val Glu Ile Lys Arg Thr Val Ala Ala Pro Ser Val
Phe Ile Phe Pro Pro Ser Asp Glu Gln Leu Lys Ser Gly Thr Ala Ser Val Val Cys Leu Leu Asn Asn
Phe Tyr Pro Arg Glu Ala Lys Val Gln Trp Lys Val Asp Asn Ala Leu Gln Ser Gly Asn Ser Gln Glu
Ser Val Thr Glu Gln Asp Ser Lys Asp Ser Thr Tyr Ser Leu Ser Ser Thr Leu Thr Leu Ser Lys Ala
Asp Tyr Glu Lys His Lys Val Tyr Ala Cys Glu Val Thr His Gln Gly Leu Ser Ser Pro Val Thr Lys
Ser Phe Asn Arg Gly Glu Cys SEQ ID NO: 10 shows the amino acid sequence of a grafted anti-TNFα Fab CDP870 heavy chain.
Glu Val Gln Leu Val Glu Ser Gly Gly Gly Leu Val Gln Pro Gly Gly Ser Leu Arg Leu Ser Cys Ala
Ala Ser Gly Tyr Val Phe Thr Asp Tyr Gly Met Asn Trp Val Arg Gln Ala Pro Gly Lys Gly Leu Glu
Trp Met Gly Trp Ile Asn Thr Tyr Ile Gly Glu Pro Ile Tyr Ala Asp Ser Val Lys Gly Arg Phe Thr
Phe Ser Leu Asp Thr Ser Lys Ser Thr Ala Tyr Leu Gln Met Asn Ser Leu Arg Ala Glu Asp Thr Ala
Val Tyr Tyr Cys Ala Arg Gly Tyr Arg Ser Tyr Ala Met Asp Tyr Trp Gly Gln Gly Thr Leu Val Thr
Val Ser Ser Ala Ser Thr Lys Gly Pro Ser Val Phe Pro Leu Ala Pro Ser Ser Lys Ser Thr Ser Gly Gly
Thr Ala Ala Leu Gly Cys Leu Val Lys Asp Tyr Phe Pro Glu Pro Val Thr Val Ser Trp Asn Ser Gly
Ala Leu Thr Ser Gly Val His Thr Phe Pro Ala Val Leu Gln Ser Ser Gly Leu Tyr Ser Leu Ser Ser
Val Val Thr Val Pro Ser Ser Ser Leu Gly Thr Gln Thr Tyr Ile Cys Asn Val Asn His Lys Pro Ser
Asn Thr Lys Val Asp Lys Lys Val Glu Pro Lys Ser Cys Asp Lys Thr His Thr Cys Ala Ala

ANALYTICAL METHOD FOR FAB AND FAB' MOLECULES

CROSS-REFERENCE TO RELATED APPLICATION

This application is the U.S. national stage application of International Patent Application No. PCT/GB2011/001135, filed Jul. 28, 2011.

The present invention relates to an improved assay method for measuring acidic species in PEGylated proteins. In particular, the present invention relates to an improved assay method for measuring acidic species for PEGylated Fab and PEGylated Fab' antibody formats.

PEGylated Fab and PEGylated Fab' antibody formats are useful in that they provide a circulating half-life in vivo similar to that of a whole antibody without the effector functions associated with a whole antibody. These formats have become useful in therapy and long term stability testing is required to support the regulatory approval process which licenses the sale of these therapeutic products. Furthermore, once approved for use by the general public manufactured product must be batch release tested before it is can be made available for sale.

The presence of acidic species in the formulations, for example after storage may be indicative of degradation (in particular deamidation) of the Fab or Fab'. Deamidation is classed by regulatory authorities as a degradation route and as such limits for the levels of deamidation are set for the product. These levels should not be exceeded during the shelf-life of the product. Whilst not wishing to be bound by theory it is thought that asparagine residues may be degraded via a succinimide intermediate by deamidation to generate acidic species, such as isoaspartic acid/aspartic acid, as set out in Scheme 1:

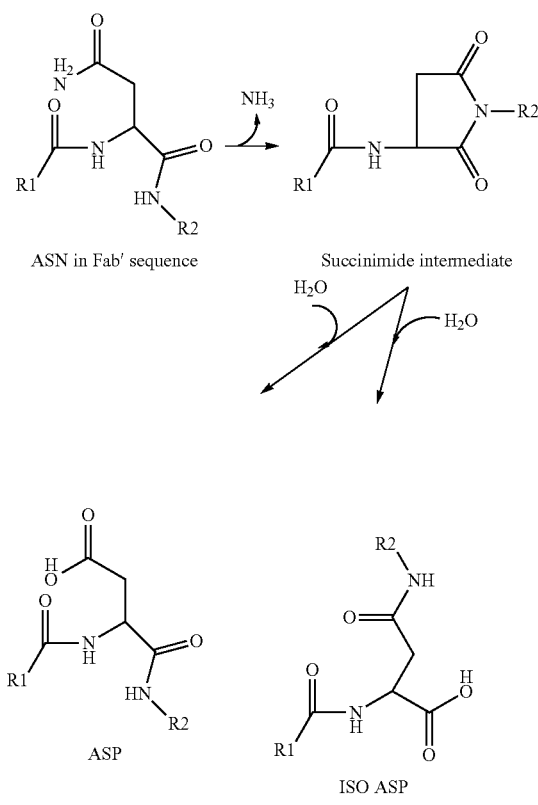

R1 & R2 are a continuation of the Fab' sequence

This deamidation of asparagine residues may result in a change in the proteins overall charge and may increase immunogenicity of the Fab or Fab'. Additionally, this deamidation may result in changes in the function/efficacy of the Fab or Fab', which may lead to unpredictable therapeutic effects/side effects or simply loss of activity. This can increase the adverse effects in patients after administration of the formulation. Thus degradation must be minimised and storage times and conditions must be limited to those when little or no degradation occurs. Therefore, it is important to be able to measure the deamidation in a given PEGylated Fab or Fab' formulation. The analysis may impact on the shelf-life and storage conditions given on the product labelling. It is also important to be able to monitor the levels of deamidation in the product because if predefined limits are exceeded then this may result in marketed products being withdrawn from sale or a block on the release for sale of certain batches of the products. In theory deamidation in the protein could be measured by quantifying the acidic species generated therein.

At the present time the total acidic species content of PEGylated Fab or PEGylated Fab' is measured using Cation Exchange (CEX)-HPLC.

The method measures an aggregate or total value of acidic species in the product. However, there are a number of routes by which the acidic species are generated and not all of those are associated with the deamidation (and hence degradation) of the protein. Thus the value obtained from the analysis is not a value for the actual amount of deamidation in the protein. In fact it includes acidic species generated by:
- degradation of the Fab' and
- hydrolysis of the linker joining the Fab' or Fab and the PEG molecule.

The hydrolysis of the PEG linker is thought to proceed through the succinimide ring as shown in FIG. 4. This hydrolysis may in fact be the dominant effect and generate a large component of the aggregate value of the acidic species when analysed. The total acidic species content is represented diagrammatically in FIG. 3, which shows acidic species generated in the protein by deamidation and acid species generated by hydrolysis of the linker. This can be represented diagrammatically as shown in FIG. 5, which shows the relative proportions of acidic species generated by hydrolysis of the linker by deamidation and a combination thereof.

The aggregate value of acidic species in a molecule is not of primary interest. Instead what is of interest is the amount of deamidation in the protein. However, the analysis of the total acidic species content does not provide a value representative of the deamidation in the protein.

The amount of deamidation can be measured, for example employing ISOQUANT® aspartate detection kits. The deamidation is represented diagrammatically in FIG. 2, which shows the deamidation in the protein only. However, this deamidation assay is not particularly robust (Alfaro et al., Anal. Chem, 2008, 80, 3882-3889).

To support the commercial manufacture of a therapeutic product, robust analytical techniques are required. The inventors believe that they have designed a robust and effective method for the analysis of the deamidation of PEGylated proteins, in particular PEGylated Fabs and Fab's.

The method of the present disclosure allows the direct measurement of acidic species in the Fab or Fab' molecule resulting from deamidation/degradation in the Fab or Fab' molecule and not in the PEG or the linker.

Thus there is provided a method of measuring acidic species generated by degradation of a Fab or Fab' component of a Fab-PEG or a Fab'-PEG comprising the steps of:

a) cleaving the PEG and linker from the Fab-PEG or Fab'-PEG with an enzyme,
b) optionally separating the PEG and linker generated in step a) from the Fab or Fab', to provide a Fab or Fab' and
c) quantitatively analyzing acidic species associated with the cleaved Fab or Fab' and/or the cleaved PEG.

By removing the PEG and linker from the Fab or Fab' the amount of deamidation in the protein can be measured by quantifying the acidic species therein. The method is reproducible and robust and furthermore the cleavage of the PEG and linker does not interfere with or change the amount of deamidation in the protein. Thus the deamidation in the cleaved Fab or Fab' should be representative of the deamidation in the protein portion of the PEGylated Fab or PEGylated Fab'.

In another embodiment the method also allows the extent of PEG linker hydrolysis to be determined by first determining the 'total' acidic species for the Fab-PEG or Fab'-PEG prior to cleavage in step (a) of the method and then subtracting the quantified acidic species associated with the Fab or Fab' component determined in step (c) of the method from the 'total' acidic species.

BRIEF DESCRIPTION OF THE FIGURES

FIG. 7 shows efficiency of a trypsin digest of a PEGylated Fab' over time.

FIG. 8 is a CEX-HPLC analysis of the crude product resulting from trypsin digest of a PEGylated Fab'.

FIG. 9 is an iCEF of a PEGylated Fab' digested by trypsin.

FIG. 10 shows sequences 1 to 9.

FIG. 11 shows sequences 10 and 11.

BRIEF DESCRIPTION OF THE SEQUENCES

Figure 1:
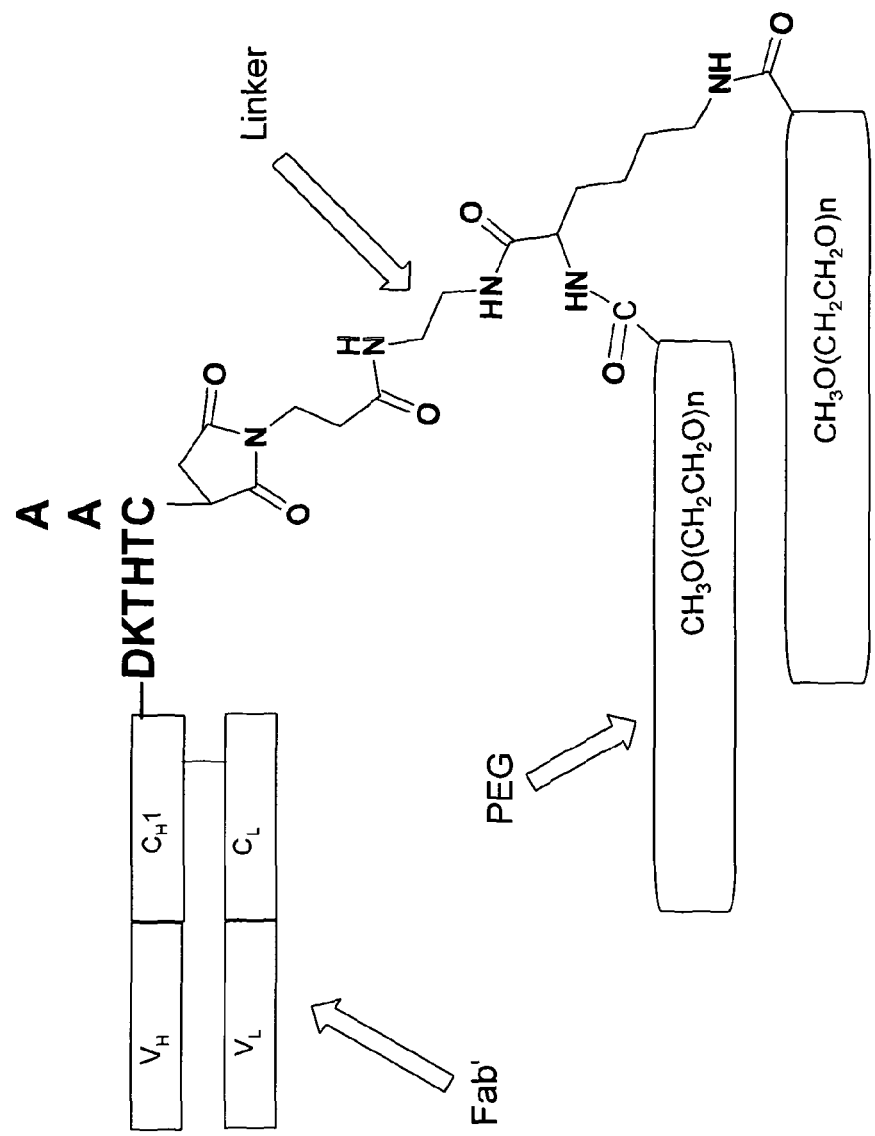
FIG. 1 shows a diagrammatic representation of a PEGylated Fab'.
Figure 2:
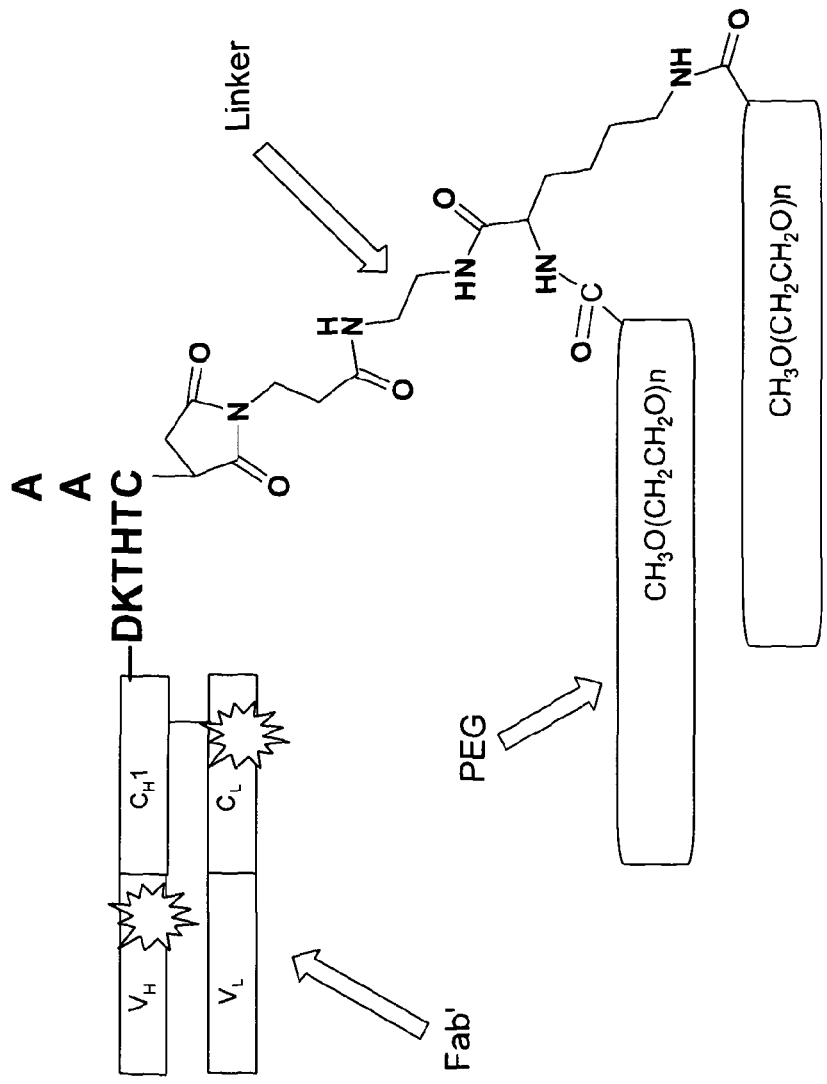
FIG. 2 shows a diagrammatic representation of deamidation occurring in a PEGylated Fab'.
Figure 3:
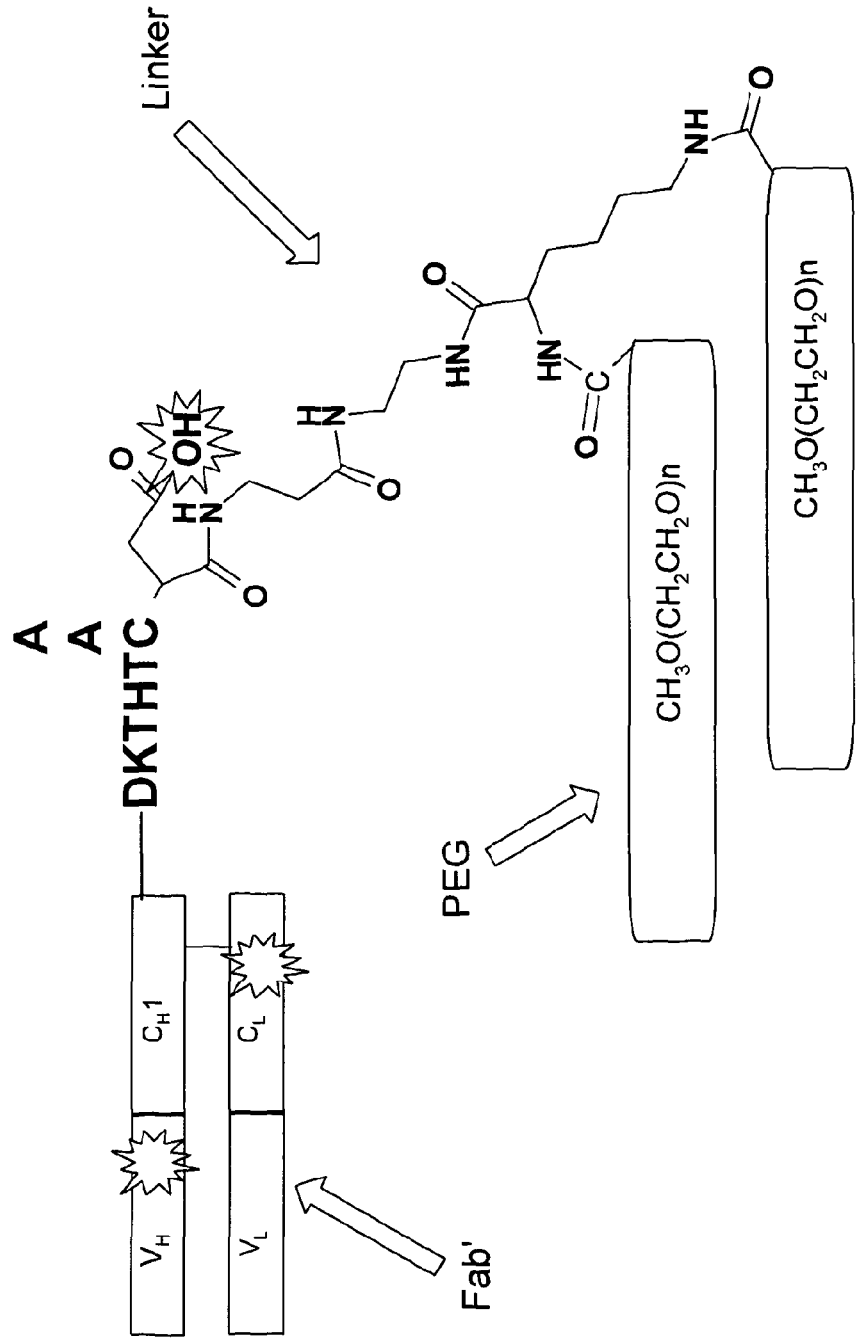
FIG. 3 shows a diagrammatic representation of deamidation and hydrolysis of the linker both of which generate acidic species.
Figure 4:
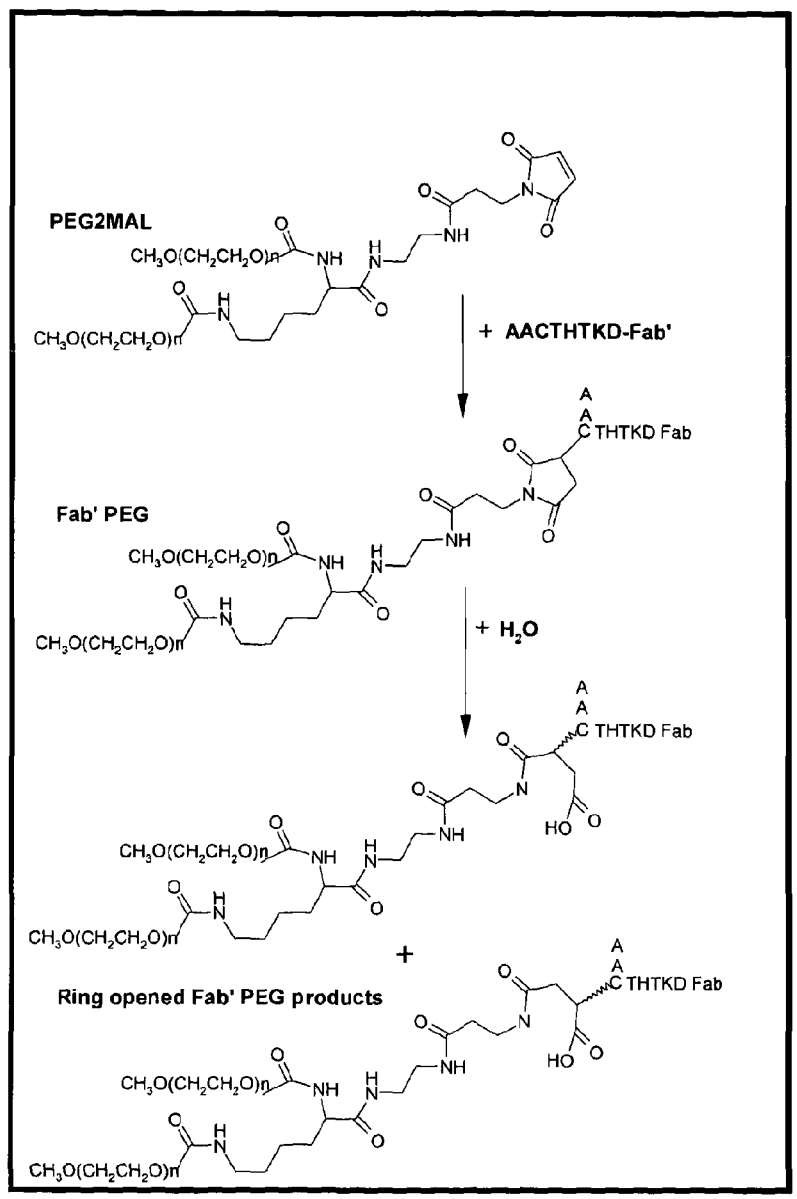
FIG. 4 shows a diagrammatic representation of the chemical process of PEGylation of a Fab' and subsequent ring opening to generate an acidic species.
Figure 5:
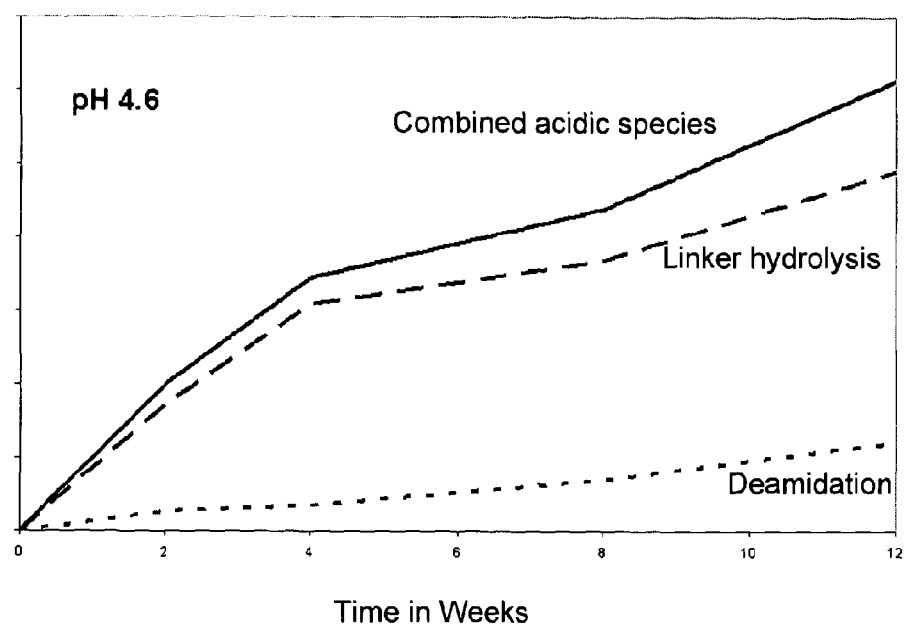
FIG. 5 is a diagrammatic representation of the relative proportions of acidic species values which contribute to the total acidic species content.
Figure 6:
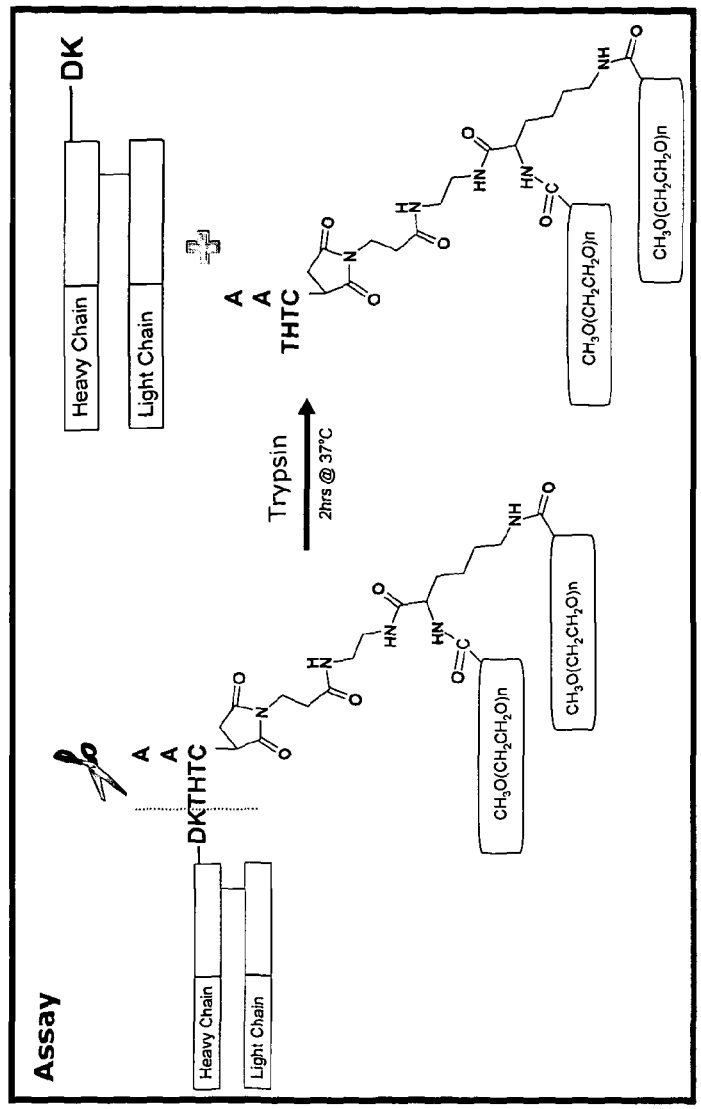
FIG. 6 is a diagrammatic representation of the species generated from a PEGylated Fab' after enzymatic digestion.

SEQ ID NO: 1 shows the amino acid sequence of CDRH1 of CDP870.
SEQ ID NO: 2 shows the amino acid sequence of CDRH2 of CDP870.
SEQ ID NO: 3 shows the amino acid sequence of CDRH3 of CDP870.
SEQ ID NO: 4 shows the amino acid sequence of CDRL1 of CDP870.
SEQ ID NO: 5 shows the amino acid sequence of CDRL2 of CDP870.
SEQ ID NO: 6 shows the amino acid sequence of CDRL3 of CDP870.
SEQ ID NO: 7 shows the nucleotide and predicted amino acid sequence of the light chain variable region CDP870.
SEQ ID NO: 8 shows the nucleotide and predicted amino acid sequence of the heavy chain variable region CDP870.
SEQ ID NO: 9 shows the amino acid sequence of a grafted anti-TNFα Fab CDP870 light chain.
SEQ ID NO: 10 shows the amino acid sequence of a grafted anti-TNFα Fab CDP870 heavy chain.

DETAILED DESCRIPTION OF THE INVENTION

Acidic species as employed herein is intended to refer to a moiety, molecule, comprising a carboxylic acid i.e. comprising the group —C(O)OH.

In one embodiment the enzyme is a protease, for example trypsin or chymotrypsin, such as trypsin. When the enzyme employed is trypsin then the cleavage point is expected to be between the K and T in, for example the sequence SCDKTH-TCAA (C-terminus Heavy Chain) of the Fab' fragment. Advantageously cleavage at that this point does not result in a change in the value of deamidation in the protein because the small portion of the hinge that is cleaved does not contain any asparagine residues.

Fab's naturally have a sequence in the hinge which is a suitable substrate for the enzyme. Fab molecules do not naturally have a substrate sequence for the enzyme but if desired an appropriate sequence can be engineered into an appropriate position allowing for removal of the PEG attached to the Fab by enzymatic digestion.

The enzymatic digestion may performed at a temperature in the range 20 to 40° C. such as 25 to 38° C., in particularly it is optimally performed at 37° C.

In one embodiment when the starting entity is a PEGylated Fab' the enzyme cleaves the hinge portion of the Fab' and releases the PEG and linker from the Fab'.

The enzymatic digestion, for example tryptic digestion may be effected over a period of 30, 40, 50, 60, 70, 80, 90, 100, 110, 120, 130, 140, 150, 160 minutes or more.

The entities generated by digestion need not be separated because if a technique such as HPLC/cIEF is employed for the quantification of acidic species the entities generated have different retention times and thus can be quantified individually without an additional separation step.

However, optionally the entities generated by step a) may be separated by known techniques, for example cation exchange chromatography, cIEF, size exclusion chromatography and the like.

In one embodiment the acidic species associated with the Fab, Fab' and/or PEG is/are quantified.

In one embodiment the deamidation of the Fab or Fab' is measured.

In one embodiment acidic species in step c) are analysed employing HPLC analysis, for example employing an elution gradient. In one embodiment the HPLC analysis is CEX-HPLC analysis.

Alternatively, the amount of deamidation in the cleaved protein may be measured by capillary electrophoresis.

In one embodiment acidic species in step c) are analysed employing cIEF analysis, suitable cartridges include iCE280 available from Convergent Bioscience.

All publications, including but not limited to patents and patent applications cited in this specification are herein incorporated by reference as if each individual publication were specifically and individually indicated to be incorporated by reference herein as though fully set forth.

In a preferred embodiment the antibody is an anti-TNF antibody, more preferably an anti-TNF Fab' CDP870, as described in WO01/094585 (the contents of which are incorporated herein by reference).

In a one embodiment the antibody having specificity for human TNFα, comprises a heavy chain wherein the variable domain comprises a CDR having the sequence shown in SEQ ID NO:1 for CDRH1, the sequence shown in SEQ ID NO:2 for CDRH2 or the sequence shown in SEQ ID NO:3 for CDRH3.

In one embodiment the antibody comprises a light chain wherein the variable domain comprises a CDR having the sequence shown in SEQ ID NO:4 for CDRL1, the sequence shown in SEQ ID NO:5 for CDRL2 or the sequence shown in SEQ ID NO:6 for CDRL3.

In one embodiment the antibody comprises a heavy chain wherein the variable domain comprises a CDR having the sequence shown in SEQ ID NO:1 for CDRH1, the sequence shown in SEQ ID NO:2 for CDRH2 or the sequence shown in SEQ ID NO:3 for CDRH3 and a light chain wherein the variable domain comprises a CDR having the sequence shown in SEQ ID NO:4 for CDRL1, the sequence shown in SEQ ID NO:5 for CDRL2 or the sequence shown in SEQ ID NO:6 for CDRL3.

In one embodiment the antibody comprises SEQ ID NO:1 for CDRH1, SEQ ID NO: 2 for CDRH2, SEQ ID NO:3 for CDRH3, SEQ ID NO:4 for CDRL1, SEQ ID NO:5 for CDRL2 and SEQ ID NO:6 for CDRL3.

The antibody is preferably a CDR-grafted antibody molecule and typically the variable domain comprises human acceptor framework regions and non-human donor CDRs.

Preferably, the antibody comprises the light chain variable domain CDP870 (SEQ ID NO:7) and the heavy chain variable domain CDP870 (SEQ ID NO:8).

It is preferred that the antibody is a modified Fab fragment wherein the modification is the addition to the C-terminal end of its heavy chain one or more amino acids to allow the attachment of an effector or reporter molecule. Preferably, the additional amino acids form a modified hinge region containing one or two cysteine residue to which the effector or reporter molecule may be attached. Such a modified Fab fragment preferably has a heavy chain comprising or consisting of the sequence given as SEQ ID NO:10 and the light chain comprising or consisting of the sequence given as SEQ ID NO:9.

The present disclosure explicitly discloses embodiment comprising certain combinations of integers. The present disclosure also extends to embodiments consisting or consisting essentially of the said combinations of integers.

Preferences and/or embodiments may be combined as technically feasible.

The invention will now be described with reference to the following examples, which are merely illustrative and should not in any way be construed as limiting the scope of the present invention.

Example

Tryptic Digestion Method

To an eppendorf, 1.0 mg Fab' PEG is added to 50 mM NaOAc, 125 mM NaCl pH 5.0 to 50 μL total volume. 50 μL 0.2M $Na_2HPO_4$ is added, followed by 40 μL trypsin resuspension buffer (50 mM Acetic Acid), the final pH should be in the region of pH 7.5. Vortex for 10 seconds.

The reaction is incubated at 37° C. for 2 hours. Analyse by CEX HPLC or imaged capillary isoelectrophoresis.

Digest Efficiency Determined by HTRP HPLC

A tryptic digest using a Fab'PEG was set up using an Agilent 1100 series auto sampler incubated at 37° C., in order that the reaction could be injected directly onto HTRP HPLC assay. 9 injections of the Fab' Peg and Fab' control were carried out sequentially. Fab' PEG gave a digest profile shown in FIG. 7. This demonstrates that within two hours, the Fab' PEG product content is reduced to ~20%.

Analysis

After digestion, samples were removed and diluted to 1 mg/mL in sample dilution buffer (20 mM Sodium Acetate pH 4.5). The Fab' PEG and cleaved Fab' can be identified along with their respective acidic species without pre-processing of the mixture obtained from the digestion step, as shown in FIG. 8. The following as shown in FIG. 8 are eluted sequentially; undigested acidic Fab' PEG species, undigested Fab' PEG, acidic cleaved Fab' species and cleaved Fab'.

Suitable Chromatographic Conditions for the Detection of Cleaved Fab' Acidic Species by CEX HPLC

| | |
|---|---|
| Solvent A | equilibration buffer 10 mM 2-(N-morpholino)Ethane Sulfonic acid pH 6.2 |
| Solvent B | elution buffer 10 mM 2-(N-morpholino)Ethane Sulfonic acid, 50 mM sodium chloride pH 6.2 |
| Column | Dionex Propac SCX-10 column |
| Flow Rate | 0.5 mL/min |
| Stop Time | 75 min |
| Max Pressure | 250 bar |
| Method Run Pressure (guide) | ~60 bar |
| Column Temperature | 25° C. |
| Injection Volume | 100 μL |
| Autosampler Temperature | 4° C. |
| Detection Wavelength | 280 nm (16 bandwidth), 4 nm slit width |
| Loading | 100 μL at 1 mg/mL |

| Time | Solvent A (%) | Solvent B (%) | Flow Rate (mL/min) |
|---|---|---|---|
| 0.0 | 100 | 0 | 0.5 |
| 2.0 | 100 | 0 | 0.5 |
| 62.0 | 40 | 60 | 0.5 |
| 62.5 | 0 | 100 | 0.5 |
| 63.5 | 0 | 100 | 0.5 |
| 64.0 | 100 | 0 | 0.5 |
| 75.0 | 100 | 0 | 0.5 |

Data Analysis may be carried out using HP Chemstation software where the peaks are integrated, see FIG. 8 for an example of chromatogram of Fab' PEG digest using the suitable chromatographic conditions described. The following are detected; undigested acidic Fab' PEG, undigested Fab' PEG, acidic cleaved Fab', cleaved Fab'.

Alternative Method of Analysis Using Imaged Capillary Isoelectrophoresis

Sample Preparation for Analysis Using iCE280

A generic sample preparation of 200 μL volume is given below:
Tryptic Digest (desalted and free from any free ions at a concentration of 1 mg/ml)-40 ul (General rule: final concentration of the protein should be around 0.1-0.3 mg/ml in final sample mixture).

1% Methyl Cellulose: 70 μL (Methyl cellulose concentration in the final the mixture should be 0.35%)

Carrier Ampholytes: (3-10 Pharmalytes)—8 μL (Carrier ampholytes should have a concentration of 4% in the final sample mix).

pI markers: 1 μL each of two different pI markers are added whose pI values should lie on the either side of the protein and its related species.

HPLC grade water: Add required amount of HPLC water to make up the volume to 200 μL.

Mix the above sample by vortexing for 15-30 second to ensure proper mixing of different components. Spin the mixture at 16000 g for 10 minutes to remove air bubbles and dust particles, which would interfere with the analysis.

Instrument Settings and Analysis Employing iCE280 Technology iCE 280 from Convergent biosciences (Isogen in Europe) is an imaged capillary isoelectrophoresis instrument, which is used to determine pIs of various protein samples and their related species.

High voltage is applied across the capillary using an anode and cathode, which are dipped, in small reservoirs containing catholyte ($OH^-$) and anolyte ($H^+$). Samples are prepared with carrier ampholytes and on application of high voltage the protein molecules migrate according to their respective pIs and finally focus at it. The anolyte may be prepared by adding calculated amount of phosphoric acid to give a final solution of 0.08 M phosphoric acid in 0.1% methyl cellulose. The catholyte may be prepared by adding 10.4 μl of 50% w/w NaOH solution to 2 ml of 0.1% methyl cellulose. Catholyte must be freshly prepared and should not be reused. Generally 2 ml is enough for a single fill of the reservoir.

Generally for all non-PEGylated samples, a focusing period of 5-6 minutes at 3000 v should be enough, but since different proteins have different charge distribution, the focusing time would also vary accordingly. In that case the settings needs to be optimised by running two or three samples.

Data analysis may be carried out using EZChrom software. Profiles can be compared by overlaying them using 'Supercompare' and electrophoregrams can be integrated using 'Method development' options within the EZChrom software. See FIG. 9 for an example of electrophoregram of Fab' PEG digest. The following are detected; low pI marker, acidic cleaved Fab' species, cleaved Fab' species, basic cleaved Fab' species, high pI marker.

The invention claimed is:

1. A method of quantitatively measuring acidic species generated by degradation of a Fab' component of a Fab'-PEG conjugate comprising the steps of:
   a) cleaving the PEG attached to said Fab' via a linker from said Fab'-PEG conjugate with an enzyme that cleaves the hinge portion of the Fab' and releases the PEG and linker from the Fab'-PEG conjugate,
   b) separating the PEG and linker generated in step a) from the Fab', to provide a Fab' and
   c) quantitatively analyzing acidic species associated with the cleaved Fab' and/or the cleaved PEG.

2. The method according to claim 1, wherein the enzyme enzyme is trypsin or chymotrypsin.

3. The method according to claim 1, wherein the cleaving in step a) is performed at a temperature in the range 25 to 40° C.

4. The method according to claim 1, wherein the cleavage of step a) occurs between a lysine and a threonine in the C-terminal portion of the Fab' heavy chain portion of the Fab'-PEG conjugate.

5. The method according to claim 4, wherein the lysine and threonine are found in the sequence SCDKTHTCAA (SEQ ID NO: 10) located at the C-terminal portion of a Fab'.

6. The method according to claim 1, wherein the separation is effected using cation exchange chromatography, cIEF, and/or size exclusion chromatography.

7. The method according to claim 1, wherein the quantification of acidic species is performed employing cation exchange chromatography or imaged capillary isoelectrophoresis.

8. The method according to claim 7, wherein said cation exchange chromatography is cation exchange HPLC (CEX-HPLC).

9. The method according to claim 1, wherein the Fab' component of said Fab'-PEG conjugate contains SEQ ID NO: 10.

10. The method according to claim 3, wherein the cleaving step in a) is performed at a temperature in the range 25° C. to 38° C.

* * * * *

UNITED STATES PATENT AND TRADEMARK OFFICE
CERTIFICATE OF CORRECTION

PATENT NO.       : 8,722,353 B2
APPLICATION NO.  : 13/812692
DATED            : May 13, 2014
INVENTOR(S)      : Bryan John Smith et al.

It is certified that error appears in the above-identified patent and that said Letters Patent is hereby corrected as shown below:

In The Specification

Column 1,
Line 22, "before it is can be" should read --before it can be--.

Column 4,
Line 16, "at that this point" should read --at this point--.
Line 26, "may performed" should read --may be performed--.

Column 7,
Line 2, "0.35%)" should read --0.35%).--.

Column 8,
Line 15, "settings needs" should read --settings need--.

In The Claims

Column 13,
Lines 57-58, "the enzyme enzyme is" should read --the enzyme is--.

Signed and Sealed this
Third Day of February, 2015

Michelle K. Lee
*Deputy Director of the United States Patent and Trademark Office*

SEQUENCE LISTING

```
<160> NUMBER OF SEQ ID NOS: 10

<210> SEQ ID NO 1
<211> LENGTH: 5
<212> TYPE: PRT
<213> ORGANISM: Artificial
<220> FEATURE:
<223> OTHER INFORMATION: Amino acid sequence of CDRH1 of CDP870

<400> SEQUENCE: 1

Asp Tyr Gly Met Asn
1               5

<210> SEQ ID NO 2
<211> LENGTH: 17
<212> TYPE: PRT
<213> ORGANISM: Artificial
<220> FEATURE:
<223> OTHER INFORMATION: Amino acid sequence of CDRH2 of CDP870

<400> SEQUENCE: 2

Trp Ile Asn Thr Tyr Ile Gly Glu Pro Ile Tyr Ala Asp Ser Val Lys
1               5                   10                  15

Gly

<210> SEQ ID NO 3
<211> LENGTH: 9
<212> TYPE: PRT
<213> ORGANISM: Artificial
<220> FEATURE:
<223> OTHER INFORMATION: Amino acid sequence of CDRH3 of CDP870

<400> SEQUENCE: 3

Gly Tyr Arg Ser Tyr Ala Met Asp Tyr
1               5

<210> SEQ ID NO 4
<211> LENGTH: 11
<212> TYPE: PRT
```

-continued

<213> ORGANISM: Artificial
<220> FEATURE:
<223> OTHER INFORMATION: Amino acid sequence of CDRL1 of CDP870

<400> SEQUENCE: 4

Lys Ala Ser Gln Asn Val Gly Thr Asn Val Ala
1               5                   10

<210> SEQ ID NO 5
<211> LENGTH: 7
<212> TYPE: PRT
<213> ORGANISM: Artificial
<220> FEATURE:
<223> OTHER INFORMATION: Amino acid sequence of CDRL2 of CDP870

<400> SEQUENCE: 5

Ser Ala Ser Phe Leu Tyr Ser
1               5

<210> SEQ ID NO 6
<211> LENGTH: 9
<212> TYPE: PRT
<213> ORGANISM: Artificial
<220> FEATURE:
<223> OTHER INFORMATION: Amino acid sequence of CDRL3 of CDP870

<400> SEQUENCE: 6

Gln Gln Tyr Asn Ile Tyr Pro Leu Thr
1               5

<210> SEQ ID NO 7
<211> LENGTH: 107
<212> TYPE: PRT
<213> ORGANISM: Artificial
<220> FEATURE:
<223> OTHER INFORMATION: Amino acid sequence of the light chain variable
      region of CDP870

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Phe Leu Tyr Ser Gly Val Pro Tyr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Leu
                85                  90                  95

Thr Phe Gly Gln Gly Thr Lys Val Glu Ile Lys
            100                 105

<210> SEQ ID NO 8
<211> LENGTH: 118
<212> TYPE: PRT
<213> ORGANISM: Artificial
<220> FEATURE:
<223> OTHER INFORMATION: Amino acid sequence of the heavy chain variable
      region of CDP870

<400> SEQUENCE: 8

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Tyr Val Phe Thr Asp Tyr
             20                  25                  30

Gly Met Asn Trp Val Arg Gln Ala Pro Gly Lys Gly Leu Glu Trp Met
         35                  40                  45

Gly Trp Ile Asn Thr Tyr Ile Gly Glu Pro Ile Tyr Ala Asp Ser Val
 50                  55                  60

Lys Gly Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
             85                  90                  95

Ala Arg Gly Tyr Arg Ser Tyr Ala Met Asp Tyr Trp Gly Gln Gly Thr
            100                 105                 110

Leu Val Thr Val Ser Ser
            115
```

```
<210> SEQ ID NO 9
<211> LENGTH: 214
<212> TYPE: PRT
<213> ORGANISM: Artificial
<220> FEATURE:
<223> OTHER INFORMATION: Amino acid sequence of a grafted anti-TNF alpha
      Fab CDP870 light chain

<400> SEQUENCE: 9
```

```
Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asn Val Gly Thr Asn
             20                  25                  30

Val Ala Trp Tyr Gln Gln Lys Pro Gly Lys Ala Pro Lys Ala Leu Ile
         35                  40                  45

Tyr Ser Ala Ser Phe Leu Tyr Ser Gly Val Pro Tyr Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ile Tyr Pro Leu
             85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210
```

```
<210> SEQ ID NO 10
<211> LENGTH: 229
<212> TYPE: PRT
<213> ORGANISM: Artificial
```

-continued

```
<220> FEATURE:
<223> OTHER INFORMATION: Amino acid sequence of a grafted anti-TNF alpha
      Fab CDP870 heavy chain

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Ala Ala
225
```